US006335384B1

(12) United States Patent
Evans et al.

(10) Patent No.: US 6,335,384 B1
(45) Date of Patent: *Jan. 1, 2002

(54) METHODS FOR EMBOLIZING BLOOD VESSELS

(75) Inventors: Scott Evans, Santa Ana, CA (US); John Perl, II, Cleveland Heights, OH (US); Richard Greff, St. Petersburg, FL (US)

(73) Assignee: Micro Therapeutics, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/680,944

(22) Filed: Oct. 10, 2000

Related U.S. Application Data

(60) Continuation of application No. 09/438,929, filed on Nov. 12, 1999, now Pat. No. 6,281,263, which is a continuation of application No. 08/868,931, filed on Jun. 4, 1997, now Pat. No. 6,017,977, which is a division of application No. 08/594,574, filed on Jan. 31, 1996, now Pat. No. 5,702,361.

(51) Int. Cl.$^7$ .......................... C08L 29/04; C08K 5/41; A61K 31/765

(52) U.S. Cl. ...................... 523/113; 523/115; 523/222; 524/173; 524/408; 424/9.1; 424/9.411; 424/423; 424/649; 424/9.42; 604/49; 604/53

(58) Field of Search ................. 604/49, 53; 424/9.1, 424/9.411, 9.42, 423, 649; 523/105, 113, 222; 524/173, 408

(56) References Cited

U.S. PATENT DOCUMENTS

| 3,527,224 A | 9/1970 | Rabinowitz et al. |
| 3,591,676 A | 7/1971 | Hawkins et al. |
| 3,711,602 A | 1/1973 | Herschler |
| 3,711,606 A | 1/1973 | Herschler |
| 4,177,267 A | 12/1979 | Herschler |
| 4,563,184 A | 1/1986 | Korol |
| 4,725,271 A | 2/1988 | Korol |
| 4,747,845 A | 5/1988 | Korol |
| 4,902,728 A | 2/1990 | Pietsch et al. |
| 4,938,763 A | 7/1990 | Dunn et al. |
| 4,997,643 A | 3/1991 | Partain, III et al. |
| 5,077,049 A | 12/1991 | Dunn et al. |
| 5,278,201 A | 1/1994 | Dunn et al. |
| 5,278,202 A | 1/1994 | Dunn et al. |
| 5,324,519 A | 6/1994 | Dunn et al. |
| 5,340,849 A | 8/1994 | Dunn et al. |
| 5,368,859 A | 11/1994 | Dunn et al. |
| 5,420,176 A | 5/1995 | Unger et al. |
| 5,580,568 A | 12/1996 | Greff et al. |
| 5,667,767 A | 9/1997 | Greff et al. |
| 5,702,361 A | * 12/1997 | Evans et al. ................. 604/53 |
| 5,718,711 A | 2/1998 | Berenstein et al. |
| 5,762,909 A | 6/1998 | Uzgiris |
| 5,894,022 A | 4/1999 | Ji et al. |

FOREIGN PATENT DOCUMENTS

| JP | 5-057014 | 3/1993 |
| JP | 5-253283 | 10/1993 |
| JP | 6-107549 | 4/1994 |

OTHER PUBLICATIONS

Casarett and Doull's *Toxicology*, Amdur et al., Editors, Pergamon Press, New York, pp. 661–664 (1975).

Castaneda–Zuniga, et al., "Part 1. Embolotherapy: Agents, Equipment, and Techniques" *Interventional Radiology*, in Vascular Embolotherapy, 2:9–32, Williams & Wilkins, Publishers (1992).

German, et al., *New England Journal of Medicine*, 250:104–106 (1954).

Hirotsune, et al., Abstract No. FO–07–03 entitled "Experimental Thrombosis of Canine Cervical Carotid Aneurysms with Interlocking Detachable coils and Cellulose Acetate Polymer", presented at *The Int'l Congress on Interventional Neuroradiology and Intravascular Neurosurgery*—Kyoto, Japan, Nov. 1995.

Hopkins, et al., "Endovascular Treatment of Aneurysms and Cerebral Vasospasms", in "Current Management of Cerebral Aneurysms", *Am. Assoc. Neuro. Surgeons*, A. Awad, Editor, Chapter II, pp. 219–242 (1993).

Kal, et al., Abstract No. FP–08–01 entitled "Cellulose Beads for a Particulate Embolic Agent—Experimental Study", presented at *The Int'l Congress on Interventional Neuroradiology and Intravascular Neurosurgery*—Kyoto, Japan, Nov. 1995.

Kinugasa, et al., "Direct Thrombosis of Aneurysms with Cellulose Acetate Polymer", *J. Neurosurg.*, 77:501–507 (1992).

Kinugasa, et al., "Early Treatment of Subarachnoid Hemorrhage After Preventing Rerupture of an Aneurysm", *J. Neurosurg.*, 83:34–41 (1995).

(List continued on next page.)

Primary Examiner—Peter Szekely
(74) Attorney, Agent, or Firm—Burns, Doane, Swecker & Mathis LLP

(57) ABSTRACT

Disclosed are methods useful for treating vascular lesions wherein a non-particulate agent such as a metal coil is introduced into a vascular site (e.g., an aneurysm cavity) in conjunction with an embolizing composition comprising a biocompatible polymer and a biocompatible solvent.

The biocompatible solvent is miscible or soluble in blood and also solubilizes the polymer during delivery. The biocompatible polymer is selected to be soluble in the biocompatible solvent but insoluble in blood. Upon contact with the blood, the biocompatible solvent dissipates from the embolic composition whereupon the biocompatible polymer precipitates. Precipitation of the polymer in the presence of the non-particular agent permits the agent to act as a structural lattice for the growing polymer precipitate.

In another embodiment, the biocompatible polymer composition can be replaced with a biocompatible prepolymer composition containing a biocompatible prepolymer.

20 Claims, No Drawings

OTHER PUBLICATIONS

Kinugasa, et al., "Prophylactic Thrombosis to Prevent New Bleeding and to Delay Aneurysm Surgery", *Neurosurg.*, 36:661 (1995).

Kondo, et al., Abstract No. FP–08–03 entitled "Subacute Macroscopic and Histological change of an Embolized Arteriovenous Malformation (AVM) with Eudragit–E", presented at *The Int'l Congress on Interventional Neuoradiology and Intravascular Neurosurgery*—Kyoto, Japan, Nov. 1995.

Mandai, et al., "Direct Thrombosis of Aneurysms with Cellulose Acetate Polymer", *J. Neurosurg.*, 77:497–500 (1992).

Matsumoto, et al., Abstract No. FP–08–04 entitled "Arteriovenous Fistula Closure with Polyurethane Coated Stent in Canine Model", presented at *The Int'l Congress on Interventional Neuroradiology and Intravascular Neurosurgery*—Kyoto, Japan, Nov. 1995.

Pruvo, et al., "Endovascular Treatment of 16 Intracranial Aneurysms with Microcoils", *Neuroradiology*, 33(suppl):S144 (Abstract) (1991).

Sheheglov, et al., Abstract No. SY–05–03 entitled Endovascular Occlusion of Intracranial Arteriovenous Malformations (AVM) by Liquid Nonadhesive Material "Embolin", presented at *The Int'l Congress on Interventional Neuroradiology and Intravascular Neurosurgery*—Kyoto, Japan, Nov. 1995.

Taki, et al., "Selection and Combination of Various Endovascular Techniques in the Treatment of Giant Aneurysms", *J. Neurosurg.*, 77:37–42 (1992).

Tokunaga, et al., Abstract No. FO–04–05 entitled "Intentionally Partial Thrombosis of Saccular Aneurysms with Cellulose Acetate Polymer (Experimental Study)", presented at *The Int'l Congress on Interventional Neuroradiology and Intravascular Neurosurgery*—Kyoto, Japan, Nov. 1995.

Wikholm, et al., Abstract No. SY–05–01 entitled "Long Time Follow Up of Patients with Cerebral Arteriovenous Malformations Embolized with NBCA", presented at *The Int'l Congress on Interventional Neuroradiology and Intravascular Neurosurgery*—Kyoto, Japan, Nov. 1995.

* cited by examiner

METHODS FOR EMBOLIZING BLOOD VESSELS

This application is a continuation of application Ser. No. 09/438,929, filed Nov. 12, 1999 now U.S. Pat. No. 6,281,263, which is a continuation of application Ser. No. 08/868,931 filed on Jun. 4, 1997, now U.S. Pat. No. 6,017,977 which in turn is a divisional of application Ser. No. 08/594,574 filed Jan. 31, 1996, now U.S. Pat. No. 5,702,361.

BACKGROUND OF THE INVENTION

Field of the Invention

This invention is directed to methods for embolizing blood vessels which methods are particularly suited for treating vascular lesions. In these methods, a non-particulate agent such as a metal coil is introduced into a vascular site (e.g., an aneurysm cavity) in conjunction with an embolizing composition comprising a biocompatible polymer and a biocompatible solvent.

The biocompatible solvent is miscible or soluble in blood and also solubilizes the polymer during delivery. The biocompatible polymer is selected to be soluble in the biocompatible solvent dissipates from the embolic composition whereupon the biocompatible polymer precipitates. Precipitation of the polymer in the presence of the non-particulate agent permits the agent to act as a structural lattice for the growing polymer precipitate.

REFERENCES

The following publications are cited in this application as superscript numbers:

[1] Castaneda-Zuniga et al., *Interventional Radiology*, in Vascular Embolotherapy, Part 1, 1:9–32, Williams & Wilkins, Publishers (1992)

[2] Hopkins, et al., "Endovascular Treatment of Aneurysms and Cerebral Vasospasms", in "Current Management of Cerebral Aneurysms", Am. Assoc. Neuro. Surgeons, A. Awad, Editor, Chapter II, pp. 219–242 (1993).

[3] Pruvo, et al., "Endovascular Treatment of 16 Intercranial Aneurysms with Microcoils", *Neuroradiology*, 33(suppl):S144 (Abstract) (1991).

[4] Mandai, et al., "Direct Thrombosis of Aneurysms with Cellulose Acetate Polymer", *J. Neurosurg.*, 77:497–500 (1992)

[5] Kinugasa, et al., "Direct Thrombosis of Aneurysms with Cellulose Acetate Polymer", *J. Neurosurg.*, 77:501–507 (1992)

[6] Casarett and Doull's *Toxicology*, Amdur et al., Editors, Pergamon Press, New York, pp. 661–664 (1975)

[7] Greff, et al., U.S. Pat. No. 5,667,767, filed as U.S. patent application Ser. No. 08/507,863 for "Novel Compositions for Use in Embolizing Blood Vessels", filed Jul. 27, 1995.

[8] Greff, et al., U.S. Pat. No. 5,580,568, filed as U.S. patent application Ser. No. 08/508,248 for "Cellulose Diacetate Compositions for Use in Embolizing Blood Vessels", filed Jul. 27, 1995.

[9] Kinugasa, et al., "Early Treatment of Subarachnoid Hemorrhage After Preventing Rerupture of an Aneurysm", *J. Neurosurg.*, 83:34–41 (1995)

[10] Kinugasa, et al., "Prophylactic Thrombosis to Prevent New Bleeding and to Delay Aneurysm Surgery", *Neurosurg.*, 36:661 (1995)

[11] Taki, et al., "Selection and Combination of Various Endovascular Techniques in the Treatment of Giant Aneurysms", *J. Neurosurg.*, 77:37–42 (1992)

[12] German, et al., *New England Journal of Medicine*, 250:104–106 (1954)

[13] Rabinowitz, et al., U.S. Pat. No. 3,527,224, for "Method of Surgically Bonding Tissues Together", issued Sep. 8, 1970

[14] Hawkins, et al., U.S. Pat. No. 3,591,676, for "Surgical Adhesive Compositions", issued Jul. 6, 1971

All of the above references are herein incorporated by reference in their entirety to the same extent as if each individual reference was specifically and individually indicated to be incorporated herein by reference in its entirety.

STATE OF THE ART

Embolization of blood vessels is conducted for a variety of purposes including the treatment of tumors, the treatment of lesions such as aneurysms, arteriovenous malformations (AVM), arteriovenous fistula (AVF), uncontrolled bleeding and the like.

Embolization of blood vessels is preferably accomplished via catheter techniques which permit the selective placement of the catheter at the vascular site to be embolized. In this regard, recent advancements in catheter technology as well as in angiography now permit neuro endovascular intervention including the treatment of otherwise inoperable lesions. Specifically, development of microcatheters and guide wires capable of providing access to vessels as small as 1 mm in diameter allows for the endovascular treatment of many lesions.

Endovascular treatment regimens include the use of non-particulate agents such as metal coils which are designed to induce thrombosis after delivery to the vascular site.[1] Ideally, after placement of the microcoils at the vascular site, thrombosis results in the formation of a clot about the coil thereby sealing the vascular site.

Complications in this procedure have, however, been reported including the fact that thrombosis about the metal coil is not uniform in nature and fragmentation of the resulting clot can occur. This former aspect can lead to incomplete sealing of, for example, vascular lesions, whereas the latter aspect can lead to migration of the blood clots in the patient's circulation.

Additionally, while platinum has been the metal of choice for use in metal coils, the thrombogenic potential of platinum coils is variable[2] and can result in incomplete sealing of the blood vessel (e.g., aneurysm). Likewise, when employed in treating aneurysms, coils are prone to migration in and/or from the aneurysm cavity after placement[2]. Coil migration away from the aneurysm cavity in such cases has been reported to result in regressive complete motor paralysis in treatment patients.[3] Likewise, migration within the aneurysm cavity prior to thrombosis can liberate calcified emboli from within the aneurysm cavity and cause intimal tears and vessel wall dissections.[2]

Still further, in the embolization of blood vessels, the choice of coil size is critical because the use of microcoils which are too small can result in coil migration within the patient's circulation and the use of coils which are too large for the blood vessel to be embolized can result in coil elongation which is recognized to be less efficient for blood vessel embolization.[1]

While efforts have been made to improve the thrombogenic properties of platinum coils by the incorporation of Dacron® threads onto the coils, coil migration remains a serious concern primarily due to potential severe adverse affects arising from such migration. Moreover, since thrombosis around the coils is essential for successful treatment of the aneurysm, care must be taken to minimize any breakage of clot fragments from the formed clot and incorporation of these fragments into the patient's circulation.

Still further, in treatment of lesions, it is common to employ multiple coils to effect thrombosis. However, the positioning and placement of multiple coils is technically challenging and often results in undesired coil migration, misplacement and/or altered shape of the coil pack.

In view of the above, there is an ongoing need to enhance the efficacy of blood vessel embolization using non-particulate agents such as metal coils.

This invention is directed to the discovery that the efficacy of blood vessel embolization via catheter delivery of microcoils and other non-particulate agents to the blood vessel site to be embolized can be enhanced by further delivering a polymer composition as described below to this site. The deposited coils or other non-particulate agents act as a lattice about which a polymer precipitate grows thereby embolizing the blood vessel.

While the use of polymer compositions to embolize blood vessels has heretofore been disclosed including compositions wherein a preformed polymer precipitates in situ from a carrier solution at the vascular site to be embolized,[4,5] such compositions invariably have been employed by themselves in the absence of non-particulate agents such as metal coils. For effective treatment, such polymer compositions must form a precipitate in the blood vessel having sufficient structural integrity to inhibit fragmentation of the precipitate and the precipitate must be anchored at the site of placement. While certain polymer compositions form precipitates having the requisite structural integrity[7,8], other polymer compositions do not. In either case, anchoring of these precipitates to the vascular site remains a serious problem particularly in lesions having high blood flow and/or diffuse necks. In such cases, precipitate anchoring to the vascular site is not an intrinsic function of the shape of the lesion to be treated and migration of the precipitate away from the intended vascular site can occur.

In view of the above, there is an ongoing need for enhancing the efficacy of polymer compositions used for embolizing vascular sites.

SUMMARY OF THE INVENTION

This invention is directed to the discovery that unexpected and surprising results are achieved when blood vessels are embolized with a combination of a non-particulate agent and a polymer composition in the manner described herein. In particulate, deficiencies associated with each of these embolizing procedures when used separately are either reduced of eliminated by using these procedures in combination. Such deficiencies addressed by this invention include, for example, (a) problems associated with variable thrombosis that the non-particulate agent at the vascular site, (b) problems associated with non-particulate agent migration after delivery to the vascular site, (c) problems associated with polymer precipitate fragmentation after precipitate formation at the vascular site, and (d) problems associated with polymer precipitate anchoring at the vascular site.

Accordingly, in one of its method aspects, this invention is directed to a method for embolizing a vascular site in a patient's blood vessel which method comprises (a) introducing, via a catheter, at the vascular site to be embolized a non-particulate agent or a plurality of said agents; and (b) delivering, via a catheter, to said vascular site a polymer composition comprising a biocompatible polymer, a biocompatible solvent and a contrast agent wherein said delivery is conducted under conditions wherein a polymer precipitate forms in situ at said vascular site thereby embolizing the blood vessel and further wherein said non-particulate agent is encapsulating within said precipitate.

In the polymer composition, the biocompatible solvent is preferably dimethyl sulfoxide (DMSO) and the biocompatible polymer is preferably an ethylene vinyl alcohol copolymer or a cellulose acetate polymer.

In another embodiment, the biocompatible polymer composition can be replaced with a biocompatible prepolymer composition containing a biocompatible prepolymer. In this embodiment, this invention is directed to a method for embolizing a vascular site in a patient's blood vessel which method comprises (a) introducing, via a catheter, at the vascular site to be embolized a non-particulate agent or a plurality, of said agents; and (b) delivering, via a catheter, to said vasculate site a prepolymer composition comprising a biocompatible prepolymer and a contrast agent wherein said delivery is conducted under conditions wherein said prepolymer polymerized in situ at said vascular site thereby embolizing the blood vessel and further wherein said non-particulate agent is encapsulated within said polymer.

In one optional embodiment, the prepolymer composition further comprises a biocompatible solvent which is preferably selected from the group consisting of dimethylsulfoxide, ethanol, and acetone.

In one of its kit aspects, this invention is directed to a kit of parts comprising:

(a) a polymer composition comprising a biocompatible polymer, a biocompatible solvent and a contrast agent; and (b) a non-particulate agent or plurality of such agents.

In another of its kit aspects, this invention is directed to a kit of parts comprising:

(a) a prepolymer composition comprising a biocompatible prepolymer and a contrast agent; and (b) a non-particulate agent or plurality of such agents.

Preferably, the kit further comprises a catheter capable of delivering said polymer composition.

In one embodiment, the catheter capable of delivering said polymer composition is the same as the catheter capable of delivering said non-particulate agent. In another embodiment, the catheter capable of delivering said polymer composition is different from the catheter capable of delivering said non-particulate agent. In this latter embodiment, the kit further comprises a catheter capable of delivering said non-particulate agent.

In another embodiment, the kit further comprises a microballoon catheter to arrest blood flow.

DETAILED DESCRIPTION OF THE INVENTION

This invention is directed to methods for embolizing vascular sites which methods incorporate both a non-particulate agent and a polymer or prepolymer composition at the vascular site to be embolized.

However, prior to discussing this invention is further detail, the following terms will first be defined:

The term "embolizing" refers to a process wherein a material is injected into a blood vessel which, in the case of for example aneurysms, fills or plugs the aneurysm sac and/or encourages clot formation so that blood flow into the aneurysm ceases, and in the case of AVM's and AVF's forms a plug or clot to control/reroute blood flow to permit proper tissue perfusion. Embolization of the blood vessel is, therefore, important in preventing/controlling bleeding due to lesions (e.g., organ bleeding, gastrointestinal bleeding, vascular bleeding as well as bleeding associated with an aneurysm). In addition, embolization can be used to ablate diseased tissue (e.g., tumors, etc.) by cutting off its blood supply.

The term "non-particulate agent" refers to biocompatible macroscopic solid materials having a discrete physical shape or structure which, when placed in a blood vessel, result in embolization of the blood vessel. The non-particulate agents are macroscopic (i.e., about 1 mm or large in size) which is contrasted with particulates which are microscopic (i.e., less than 1 mm in size). Examples of such non-particulate agents include, coils (including metallic coils, coils with barbs, etc.), silk streamers, plastic brushes, detachable balloons (e.g., silicon or latex balloons), foam (e.g., polyvinyl alcohol foam), nylon mesh and the like. Such non-particulate agents are generally commercially available. For example, platinum coils are available from Target Therapeutics, San Jose, Calif., U.S.A.

The specific non-particulate agent employed is not critical and preferred agents include metallic coils, metallic coils with barbs, metallic coils with fibers (e.g., Dacron® wool fibers) and/or streamers, etc. More preferably, platinum coils are employed.

The term "biocompatible polymer" refers to polymers which, in the amounts employed, are non-toxic, chemically inert, and substantially non-immunogenic when used internally in the patient and which are substantially insoluble in blood. Suitable biocompatible polymers include, by way of example, cellulose acetates[5,9-10] (including cellulose diacetate[8]), ethylene vinyl alcohol copolymers[7,11], hydrogels (e.g., acrylics), polyacrylonitrile and the like. Preferably, the biocompatible polymer is also non-inflammatory when employed in situ.

The particulate biocompatible polymer employed is not critical and is selected relative to the viscosity of the resulting polymer solution, the solubility of the biocompatible polymer in the biocompatible solvent, the compatibility of the polymer composition with the non-particulate agent and the like. Such factors are well within the skill of the art.

Preferred biocompatible polymers include cellulose diacetate and ethylene vinyl alcohol copolymer. Cellulose diacetate polymers are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to 64,000. The weight average molecular weight of the cellulose diacetate composition, as determined by gel permeation chromatography, is preferably from about 50,000 to 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by mere adjustment of the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the embolizing properties of the composition. Such additional monomers include, by way of example only, maleic anhydride, styrene, propylene, acrylic acid, vinyl acetate and the like.

Ethylene vinyl alcohol copolymers are either commercially available or can be prepared by art recognized procedures. Preferably, the ethylene vinyl alcohol copolymer composition is selected such that a solution of 6 weight percent of the ethylene vinyl alcohol copolymer, 35 weight percent of a tantalum contrast agent in DMSO has a viscosity equal to or less than 60 centipoise at 20° C. As is apparent to one skilled in the art, with all other factors being equal, copolymers having a lower molecular weight will impart a lower viscosity to the composition as compared to higher molecular weight copolymers. Accordingly, adjustment of the viscosity of the composition as necessary for catheter delivery can be readily achieved by mere adjustment of the molecular weight of the copolymer composition.

As is also apparent, the ratio of ethylene to vinyl alcohol in the copolymer affects the overall hydrophobicity/hydrophilicity of the composition which, in turn, affects the relative water solubility/insolubility of the composition as well as the rate of precipitation of the copolymer in an aqueous solution (e.g., blood). In a particularly preferred embodiment, the copolymers employed herein comprise a mole percent of ethylene of from about 25 to about 60 and a mole percent of vinyl alcohol of from about 40 to about 75. These compositions provide for requisite precipitate rates suitable for use in embolizing blood vessels.

The term "contrast agent" refers to a radiopaque material capable of being monitored during injection into a mammalian subject by, for example, radiography. The contrast agent can be either water soluble or water insoluble. Examples of water soluble contrast agents include metrizamide, iopamidol, iothalamate sodium, iodomide sodium, and meglumine. Examples of water insoluble contrast agents include tantalum, tantalum oxide and barium sulfate, each of which is commercially available in the proper form for in vivo use including a particle size of about 10 $\mu$m or less. Other water insoluble contrast agents include gold, tungsten and platinum.

Preferably, the contrast agent is water insoluble (i.e., has a water solubility of less than 0.01 mg/lml at 20° C.).

The term "biocompatible solvent" refers to an organic material liquid at least at body temperature of the mammal in which the biocompatible polymer is soluble and, in the amounts used, is substantially non-toxic. Suitable biocompatible solvents include, by way of example, dimethylsulfoxide, analogues/homologues of dimethylsulfoxide, ethanol, acetone, and the like. Aqueous mixtures with the biocompatible solvent can also be employed provided that the amount of water employed is sufficiently small that the dissolved polymer precipitates upon contact with the blood. Preferably, the biocompatible solvent is dimethylsulfoxide.

The term "encapsulation" as used relative to the contrast agent and/or non-particulate agent being encapsulated in the polymer precipitate is not meant to infer any physical entrapment of the contrast agent within the precipitate much as a capsule encapsulates a medicament. Rather, this term is used to mean that an integral coherent precipitate forms which does not separate into individual components.

The term "biocompatible prepolymer" refers to materials which polymerize in situ to form a polymer and which, in the amounts employed, are non-toxic, chemically inert, and substantially non-immunogenic when used internally in the patient and which are substantially insoluble in blood. Suitable biocompatible prepolymers include, by way of example, cyanoacrylates[1,13,14], hydroxyethyl methyacrylate, silicon prepolymers, and the like. The prepolymer can either be a monomer or a reactive oligomer[13]. Preferably, the biocompatible prepolymer is also non-inflammatory when employed in situ.

Compositions

The polymer or prepolymer compositions employed in the methods of this invention are prepared by conventional methods whereby each of the components is added and the resulting composition mixed together until the overall composition is substantially homogeneous.

For example, polymer compositions can be prepared by adding sufficient amounts of the biocompatible polymer to the biocompatible solvent to achieve the effective concentration for the polymer composition. Preferably, the polymer composition will comprise from about 2.5 to about 8.0 weight percent of the biocompatible polymer composition based on the total weight of the polymer composition and more preferably from about 4 to about 5.2 weight percent. If necessary, gentle heating and stirring can be used to effect dissolution of the biocompatible polymer into the biocompatible solvent, e.g., 12 hours at 50° C.

Sufficient amounts of the contrast agent are then added to the solution to achieve the effective concentration for the complete polymer composition. Preferably, the polymer composition will comprise from about 10 to about 40 weight percent of the contrast agent and more preferably from about 20 to about 40 weight percent and even more preferably 35 weight percent. When the contrast agent is not soluble in the biocompatible solvent, stirring is employed to effect homogeneity of the resulting suspension. In order to enhance formation of the suspension, the particle size of the contrast agent is preferably maintained at about 10 µm or less and more preferably at from about 1 to about 5 µm (e.g., an average size of about 2 µm).

The particulate order of addition of components to the biocompatible solvent is not critical and stirring of the resulting suspension is conducted as necessary to achieve homogeneity of the composition. Preferably, mixing/stirring of the composition is conducted under an anhydrous atmosphere at ambient pressure. The resulting composition is heat sterilized and then stored preferably in sealed amber bottles or vials until needed.

Prepolymer compositions can be prepared by adding sufficient amounts of the contrast agent to the solution to achieve the effective concentration for the complete polymer composition. Preferably, the prepolymer composition will comprise from about 10 to about 40 weight percent of the contrast agent and more preferably from about 20 to about 40 weight percent and even more preferably 35 weight percent. When the contrast agent is not soluble in the biocompatible prepolymer composition, stirring is employed to effect homogeneity of the resulting suspension. In order to enhance formation of the suspension, the particle size of the contrast agent is preferably maintained at about 10 µm or less and more preferably at from about 1 to about 5 µm (e.g., an average size of about 2 µm).

When the prepolymer is liquid (as in the case of polyurethanes), the use of a biocompatible solvent is not absolutely necessary but may be preferred to provide for an appropriate viscosity, etc. in the embolic composition. Preferably, when employed, the biocompatible solvent will comprise from about 50 to about 90 weight percent of the biocompatible prepolymer composition based on the total weight of the prepolymer composition and more preferably from about 60 to about 80 weight percent.

In a particularly preferred embodiment, the prepolymer is cyanoacrylate which is preferably employed in the absence of a biocompatible solvent. When so employed, the cyanoacrylate adhesive is selected to have a viscosity of from about 5 to about 20 centipoise at 20° C.

The particular order of addition of components is not critical and stirring of the resulting suspension is conducted as necessary to achieve homogeneity of the composition. Preferably, mixing/stirring of the composition is conducted under an anhydrous atmosphere at ambient pressure. The resulting composition is sterilized and then stored preferably in sealed amber bottles or vials until needed.

Methods

The composition described above are then employed in methods for embolizing mammalian blood vessels. In these methods, the non-particulate agent (e.g., platinum coils) is first introduced to the vascular site to be embolized via conventional catheter technology. See, for example, Hopkins et al.[2] for a discussion of conventional catheter techniques for introduction of such agents into the vascular site.

After introduction of the non-particulate agent to the vascular site, a sufficient amount of the polymer composition is introduced by conventional means (e.g., catheter delivery under fluoroscopy). Upon discharge of the polymer composition from the catheter into the vascular site, the biocompatible solvent dissipates into the blood resulting in precipitation of the biocompatible polymer. The precipitate forms around the non-particulate agent which acts as a lattice for precipitate growth and eventual blood vessel embolization. In turn, the non-particulate agent anchors the growing precipitate to the vascular site and is selected relative to its ability to remain at the vascular site.

The particulate amount of polymer composition employed in dictated by the total volume of the vasculature to be embolized, the concentration of polymer in the composition, the rate of precipitate (solids formation) of the polymer, the size and number of non-particulate agent employed, etc. Such factors are well within the skill of the art. For example, the rate of precipitation can be controlled by changing the overall hydrophobicity/hydrophilicity of the polymer with faster precipitation rates being achieved by a more hydrophobic polymer composition.

The particulate combination of non-particulate agent and polymer composition employed is governed by the compatibility of these materials with each other. Each component is deemed compatible if it is essentially inert in the presence of the other components. For example, when dimethyl sulfoxide is employed as the biocompatible solvent in the polymer composition, the non-particulate agent is selected to be compatible with this solvent. Accordingly, plastic, wool and wood coils would typically not be employed in combination with such a polymer composition insofar as such coils may degrade in the presence of dimethyl sulfoxide. Contrarily, platinum coils are essentially inert in the presence of dimethyl sulfoxide and, accordingly, such a combination would be compatible.

One particularly preferred method for delivering the non-particulate agent and the polymer composition to the selected vascular site is via a small diameter medical catheter. The particulate catheter employed is not critical provided that polymeric catheter components are compatible with the polymeric composition (i.e., the catheter components will not readily degrade in the polymer composition and none of the components of the polymer compositions will readily degrade in the presence of the catheter components). In this regard, it is preferred to use polyethylene in the catheter components because of its inertness in the presence of the polymeric composition described herein. Other materials compatible with the embolizing compositions can be readily determined by the skilled artisan and include, for example, other polyolefins, fluoropolymers (e.g., Teflon™), silicone, etc.

When delivered by catheter, the injection rate of the polymer composition dictates, in part, the form of the precipitate at the vascular site. Specifically, low injection rates of approximately 0.05 to 0.3 cc/minute will provide for a precipitate in the form of a kernel or nodule which is particularly beneficial for site specific embolization (e.g., aneurysms) because the precipitate forms primarily at the point of injection. Contrarily, high injection rates of about 0.1 to 0.5 or more cc/several seconds (e.g., up to 10 seconds) will provide for a filament like mass projecting downstream from the catheter tip which is particularly beneficial for providing the embolizing agent deep into the vascular tree. Such procedures are suitable for embolizing tumor masses and organs.

When introduced into the vascular site, the non-particulate agent may become fixed against the vascular wall thereby anchoring the embolic site. Addition of the polymer composition to this site results in rapid diffusion of the biocompatible solvent into the blood and a solid-precipitate forms which precipitate is the biocompatible polymer/contrast agent with the non-particulate agent encapsulated therein. Without being limited to any theory, it is believed that initially, a soft gel to spongy solid precipitate forms upon contract with the blood and non-particulate agent which precipitate is open and fibrous in structure and forms around the non-particulate agent. This precipitate then restricts blood flow, entrapping red cells thereby causing clot embolization of the blood vessel.

Without being limited to any theory, the methods of this invention address the prior art problems recited above because problems associated with variable thrombosis about the non-particulate agent at the vascular site are reduced because this agent is encapsulated in the polymer precipitate are further because this agent is not the only thrombic agent employed to effect embolization but rather is employed in conjunction with the polymer precipitate. Also, encapsulation of the non-particulate agent in the polymer composition minimizes migration of these agents. Additionally, since the non-particulate agent acts as a structural lattice, the structural integrity of the precipitate is enhanced thereby minimizing fragmentation. Lastly, because the non-particulate agent acts as an appropriate anchor, the precipitate is held in position more effectively than if only the polymer composition was employed to embolize the blood vessel.

The methods described herein can also employ a biocompatible prepolymer such as cyanoacrylate in place of or in conjunction with the polymer composition described above. When the prepolymer is liquid (as in the case of cyanoacrylates), the use of a biocompatible solvent is not absolutely necessary but may be preferred to provide for an appropriate viscosity, etc. in the embolic composition. Upon injection into the vascular site, the prepolymer will polymerize in situ upon contact with the blood and form a solid polymer around the non-particulate agent thereby encapsulating this agent in the polymer and embolizing the blood vessel.

For polymer compositions, the methods of this invention are conveniently practiced by use of a kit of parts comprising:

(a) a polymer composition comprising a biocompatible polymer, a biocompatible solvent and a contrast agent; and (b) a non-particulate agent or plurality of such agents.

For prepolymer compositions, the methods of this invention are conveniently practiced by use of a kit of parts comprising:

(a) a prepolymer composition comprising a biocompatible prepolymer and a contrast agent; and (b) a non-particulate agent or plurality of such agents.

Preferably, in either case, the kit further comprises a catheter capable of delivering said polymer or prepolymer composition.

In one embodiment, the catheter capable of delivering said polymer or prepolymer composition is the same as the catheter capable of delivering said non-particulate agent. In another embodiment, the catheter capable of delivering said polymer or prepolymer composition is different from the catheter capable of delivering said non-particulate agent. In this latter embodiment, the kit further comprising a catheter capable of delivering said non-particulate agent.

In another embodiment, the kit further comprises a microballoon catheter to arrest blood flow.

Utility

The methods described herein are useful in embolizing mammalian blood vessels which, in turn, can be used to prevent/control bleeding due to lesions (e.g., organ bleeding, gastrointestinal bleeding, vascular bleeding, bleeding associated with an aneurysm) or to ablate diseased tissue (e.g., tumors, etc.). Accordingly, these methods find use in human and other mammalian subjects requiring embolization of blood vessels.

The kit of parts described herein find particulate utility for use with these methods because the kit conveniently provides all of the components required to practice the described methods.

It is contemplated that the methods described herein can also be employed non-vascularly, for example, in fallopian tubes or the vas deferens to effect female and male sterilization respectively.

The following examples are set forth to illustrate the claimed invention and are not to be construed as a limitation thereof.

EXAMPLES

Unless otherwise stated, all temperatures are in degrees Celsius. Also, in these examples and elsewhere, the following abbreviations have the following meanings:

| cc | = | cubic centimeter |
|---|---|---|
| DMSO | = | dimethylsulfoxide |
| EVOH | = | ethylene vinyl alcohol copolymer |
| mm | = | millimeter |
| μm | = | micron |

In the following examples, Examples 1–2 illustrate the preparation of polymer compositions useful in the methods described herein which polymer compositions comprise cellulose acetate and EVOH. Examples 3 and 4 illustrate how such polymer compositions could be used in the methods of this invention.

Example 1

A cellulose diacetate polymer composition was prepared by dissolving cellulose acetate (39.7 weight percent acetyl content) into DMSO to provide for an 6.8 weight percent concentration of the copolymer in DMSO. To this solution was added either tantalum (10 weight percent, available from Leico Industries, New York, N.Y., U.S.A., 99.95% purity, less than 43 µm in size) or metrizamide (38.5 weight percent, available from Aldrich Chemical Company, Milwaukee, Wis., U.S.A.) as a water soluble contrast agent.

In the tantalum composition, tantalum settling can result from prolonged standing. Sonification may help but thorough mixing prior to use is required.

Example 2

An EVOH polymer composition was prepared by dissolving EVOH (44 mole percent ethylene) into DMSO to provide for an 6.8 weight percent concentration of the copolymer in DMSO. In order to facilitate dissolution, the system can be heated to 50° C. overnight.

To this solution was added either tantalum (10 weight percent, available from Leico Industries, New York, N.Y., U.S.A., 99.95% purity, less than 43 µm in size) as a water soluble contrast agent or metrizamide (38.5 weight percent, available from Aldrich Chemical Company, Milwaukee, Wis., U.S.A.) as a water soluble contrast agent.

In the tantalum composition, tantalum settling can result from prolonged standing. Sonification may help but thorough mixing prior to use is required.

Example 3

The purpose of this example is to illustrate how an in vivo application of the methods of this invention in the embolization of a blood vessel could be accomplished.

In this example, a 50 pound male hound is prepared for blood vessel embolization using an embolic composition comprising 5.8 weight percent EVOH polymer (containing 48 weight percent ethylene), 20 weight percent tantalum in DMSO. This composition is loaded into a syringe and embolization of the left kidney is proceeded by placement of a 3F micro catheter into the kidney through a 5F AngioDynamics Headhunter catheter. The catheter is advanced into the renal artery, flushed with contrast agent to identify the location. Platinum coils are then delivered into the renal artery via the catheter followed by flushing with DMSO. The EVOH polymer composition (0.3 cc) is then delivered to this vascular site. The EVOH composition is quickly injected into the renal artery. After delivery, the DMSO is the EVOH composition rapidly diffuses and the EVOH precipitates around the platinum coil resulting in embolization of the upper pole of the kidney.

Example 4

The purpose of this example is to illustrate how an in vivo application of the methods of this invention in the treatment of an aneurysm could be accomplished.

A 10–15 kg mongrel dog is anesthetized. Under sterile conditions and with the aid of an operating microscope, an experimental aneurysm is surgically created in the carotid artery using a jugular vein pouch, employing the method of German et al.[12] After about one week, the aneurysm is embolized with a combination of microcoils and liquid embolic composition.

Specifically, the femoral arteries are accessed by cut down and introducers and 7 Fr guiding catheters are placed. Microcoils are introduced into the aneurysm by placing a microcatheter (e.g., Tracker® and guide wire) through the guiding catheter and positioning the catheter tip into the aneurysm under fluoroscopic guidance. One or more platinum microcoils are pushed through the microcatheter into the aneurysmal sac, where they are disengaged and deposited. Flushing with contrast solution confirms microcoil placement. The microcatheter is removed.

For deposition of the liquid polymer composition, a microcatheter (e.g., Tracker 18®, with guide wire) is placed through the guiding catheter and is positioned under fluoroscopic guidance so that the catheter tip is in the aneurysmal sac. A microballoon catheter (4–5 mm balloon) is placed in the carotid artery proximal to the aneurysm. Position is confirmed with injection of contrast agent. The balloon is inflated to slow or arrest blood flow to prevent displacement of the liquid polymer composition during injection.

Approximately 0.3 to 0.5 cc of liquid polymer composition is injected into the aneurysm over 1 to 2 minutes to fill the aneurysm space. Care is given not to overfill the aneurysm and block the parent artery with polymer. Filling is easily visualized with fluoroscopy due to the presence of contrast agent in the polymer composition. After about 5 minutes, the polymer is fully precipitated and the catheters are removed from the artery.

It is understood that the same procedures set forth above can be employed with compositions employing liquid prepolymers. However, when so employed, the timing and injection rates will vary depending on the cure rate for the prepolymer. Such factors are within the skill of the art.

From the foregoing description, various modifications and changes in the composition and method will occur to those skilled in the art. All such modifications coming within the scope of the appended claims are intended to be included therein.

What is claimed is:

1. A method for embolizing a vascular site in a patient's blood vessel which method comprises
    (a) introducing, via a catheter, at the vascular site to be embolized a non-particulate agent or a plurality of said agents;
    (b) delivering, via a catheter, to said vascular site a polymer composition comprising a biocompatible polymer, dimethyl sulfoxide and a water insoluble contrast agent
wherein said delivery is conducted under conditions wherein a polymer precipitate forms in situ at said vascular site thereby embolizing the blood vessel and further wherein said non-particulate agent acts as a structural lattice for precipitate growth.

2. The method according to claim 1 wherein said water insoluble contrast agent is selected from the group consisting of tantalum, tantalum oxide, tungsten and barium sulfate.

3. A method for embolizing an aneurysm in a mammalian patient which method comprises
    (a) introducing, via a catheter, into the aneurysm cavity a metallic coil or a plurality of metallic coils;
    (b) delivering, via a catheter, to said cavity a polymer composition comprising ethylene vinyl alcohol copolymer, dimethyl sulfoxide and a water insoluble contrast agent selected from the group consisting of tantalum, tantalum oxide, tungsten and barium sulfate
wherein said delivery is conducted under conditions wherein a polymer precipitate forms in situ in the aneurysm cavity thereby blocking the aneurysm and further wherein said metallic coil acts as a structural lattice for precipitate growth.

4. The method according to claim 3 wherein said water insoluble contrast agent is tantalum.

5. The method according to claim 3 wherein the polymer composition is injected into the aneurysm at a rate of about 0.05 to 0.3 cc/minute.

6. The method according to claim 3 wherein the polymer composition is injected into the aneurysm at a rate of at least 0.6 cc/minute.

7. A method for embolizing a vascular site in a patient's blood vessel which method comprises (a) introducing, via a catheter, at the vascular site to be embolized a non-particulate agent or a plurality of said agents; and (b) delivering, via a catheter, to said vascular site a prepolymer composition comprising a biocompatible prepolymer and a water insoluble contrast agent wherein said delivery is conducted under conditions wherein said prepolymer polymerizes in situ in said vascular site thereby embolizing the blood vessel and further wherein said non-particulate agent acts as a structural lattice for solid polymer formation.

8. The method according to claim 7 wherein said prepolymer composition further comprises a biocompatible solvent.

9. The method according to claim 8 wherein said biocompatible solvent is selected from the group consisting of dimethylsulfoxide, ethanol, and acetone.

10. A method for embolizing a vascular site in a patient's blood vessel which method comprises (a) introducing, via a catheter, at the vascular site to be embolized a non-particulate agent or a plurality of said agents;

(b) delivering, via a catheter, to said vascular site a polymer composition comprising a biocompatible polymer, dimethyl sulfoxide and a water insoluble contrast agent wherein said delivery is conducted under conditions wherein a polymer precipitate forms in situ at said vascular site thereby embolizing the blood vessel and further wherein said non-particulate agent becomes fixed against a vascular wall thereby anchoring an embolic site.

11. The method according to claim 10 wherein said water insoluble contrast agent is selected from the group consisting of tantalum, tantalum oxide, tungsten and barium sulfate.

12. The method according to claim 10 wherein said non-particulate agent is a metallic coil or a plurality of metallic coils.

13. The method according to claim 12 wherein said metallic coil is a platinum coil.

14. A method for embolizing an aneurysm in a mammalian patient which method comprises (a) introducing, via a catheter, into the aneurysm cavity a metallic coil or a plurality of metallic coils;

(b) delivering, via a catheter, to said cavity a polymer composition comprising a ethylene vinyl alcohol copolymer, dimethyl sulfoxide and a water insoluble contrast agent selected from the group consisting of tantalum, tantalum oxide, tungsten and barium sulfate wherein said delivery is conducted under conditions wherein a polymer precipitate forms in situ in the aneurysm cavity thereby blocking the aneurysm and further wherein said metallic coil becomes fixed against a vascular wall thereby anchoring an embolic site.

15. The method according to claim 14 wherein said water insoluble contrast agent is tantalum.

16. The method according to claim 14 wherein the polymer composition is injected into the aneurysm at a rate of about 0.05 to 0.3 cc/minute.

17. The method according to claim 14 wherein the polymer composition is injected into the aneurysm at a rate of at least 0.6 cc/minute.

18. A method for embolizing a vascular site in a patient's blood vessel which method comprises (a) introducing, via a catheter, at the vascular site to be embolized a non-particulate agent or a plurality of said agents; and (b) delivering, via a catheter, at the vascular site a prepolymer composition comprising a biocompatible prepolymer and a water insoluble contrast agent wherein said delivery is conducted under conditions wherein said prepolymer polymerizes in situ at said vascular site thereby embolizing the blood vessel and further wherein said non-particulate agent becomes fixed against a vascular wall thereby anchoring an embolic site.

19. The method according to claim 18 wherein said prepolymer composition further comprises a biocompatible solvent.

20. The method according to claim 19 wherein said biocompatible solvent is selected from the group consisting of dimethylsulfoxide, ethanol, and acetone.

* * * * *